United States Patent
Eisenmann et al.

(10) Patent No.: US 7,154,593 B2
(45) Date of Patent: Dec. 26, 2006

(54) METHOD AND APPARATUS FOR MEASURING BLOOD SUGAR

(75) Inventors: Martin Eisenmann, Ottobrunn (DE); Norbert Pöllmann, Eching (DE); Ernst Markart, München (DE)

(73) Assignee: LRE Technology Partner GmbH, Munich (DE)

( * ) Notice: Subject to any disclaimer, the term of this patent is extended or adjusted under 35 U.S.C. 154(b) by 0 days.

(21) Appl. No.: 10/885,943

(22) Filed: Jul. 6, 2004

(65) Prior Publication Data

US 2004/0252292 A1    Dec. 16, 2004

Related U.S. Application Data

(63) Continuation of application No. 10/294,226, filed on Nov. 14, 2002, now Pat. No. 6,825,918.

(30) Foreign Application Priority Data

Nov. 20, 2001   (DE)   ................. 101 56 809

(51) Int. Cl.
*G01N 33/48*   (2006.01)

(52) U.S. Cl. ........................................ 356/39

(58) Field of Classification Search ............... None
See application file for complete search history.

(56) References Cited

U.S. PATENT DOCUMENTS

| | | | |
|---|---|---|---|
| 5,770,389 A * | 6/1998 | Ching et al. | 435/7.92 |
| 5,889,585 A | 3/1999 | Markart | |
| 6,055,060 A * | 4/2000 | Bolduan et al. | 356/433 |
| 6,441,898 B1 * | 8/2002 | Markart | 356/244 |
| 6,445,451 B1 | 9/2002 | Douglas-Hamilton | |
| 6,541,266 B1 | 4/2003 | Modzelewski | |
| 6,574,425 B1 | 6/2003 | Weiss | |
| 2002/0146835 A1 * | 10/2002 | Modzelewski et al. | 436/95 |

* cited by examiner

*Primary Examiner*—Michael P. Stafira
(74) *Attorney, Agent, or Firm*—McCormick, Paulding & Huber LLP

(57) ABSTRACT

In a method for the measurement of the concentration of a substance in a liquid, especially for blood sugar measurement, the liquid to be measured is applied to the measuring field of a test strip, which measuring field is composed of a hydrophilic material, and the change of the optical reflectivity or transmissivity effected thereby in the area of the measuring field is captured. A measured value taken after a pre-given time is compared with a reference value and an indication is made if a relationship of the measured value to the reference value exceeds a pre-given threshold value.

10 Claims, 2 Drawing Sheets

METHOD AND APPARATUS FOR MEASURING BLOOD SUGAR

CROSS REFERENCE TO RELATED APPLICATION

This application is a continuation application of U.S. patent application Ser. No. 10/294,226 filed on Nov. 14, 2002 now U.S. Pat. No. 6,825,918 and entitled "Method and Apparatus for Measuring Blood Sugar", the disclosure of which is incorporated herein by reference. Applicants hereby claim foreign priority under 35 U.S.C. § 119 from German Application No. 101 56 839.6 filed 20 Nov. 2001, the disclosure of which is herein incorporated by reference.

FIELD OF THE INVENTION

The invention concerns a method for the measurement of the concentration of a substance in a liquid, especially for blood sugar measurement, wherein the liquid to be measured is applied to the measuring field of a test strip, which measuring field is composed of a hydrophilic material, and the change of the optical reflectivity or transmissivity thereby effected in the area of the measuring field is captured.

BACKGROUND OF THE INVENTION

In the case of a blood sugar measurement carried out by a patient himself or herself, the patient supplies a drop of blood to the test field of a test strip which is then optically measured, with a detector for example capturing the change in color of the measuring field, which change in color is evoked by the application of the blood to the test field. The signal given by the detector corresponds to an average value of the color change in the test field. A correct value is then only obtained if the amount of blood is sufficient to uniformly wet the entire measuring field. On the other hand, if the measuring field is only partially wetted, the measurement is falsified in that in the communication of the measured value areas are included in which practically no chemical reaction has taken place and accordingly no color change has occurred. By the time this fault is recognized in a customary measurement as a rule no subsequent dosing is any longer possible, because in the wetted portion of the measuring field the chemical reaction already has advanced too far and even with a further dropping of blood a uniform discoloration of the measuring field can no longer be obtained. Moreover, as rule on the part of the patient the small puncture wound out of which the blood drop has been pressed has again so far closed that no further blood escapes. The patient must therefore repeat the measurement, which for him or her is very unpleasant when one remembers that a patient, depending on circumstances, may have to carry out such measurement several times a day and each time has to stick himself or herself in a finger.

SUMMARY OF THE INVENTION

The invention has as its object the provision of a method of the aforegoing type in which the previously mentioned fault is timely recognized and can be overcome in the same measuring procedure.

This object is solved in accordance with the invention in that the measured value obtained after a pre-given time is compared with a reference value and in that an indication is made if a relationship of the measured value to the reference value exceeds a pre-given threshold value.

With a normal amount of liquid, that is a sufficient amount of liquid for carrying out the measurement correctly and a low content of the to be measured substance, after a given reaction time a minimum amount of discoloration, depending on the type of the test strip (corresponding to an upper reflectivity limit) is achieved. If the reflectivity lies above this limit value the measuring field is presumed to have not been sufficiently wetted with the investigated liquid, that is an under-dosing has occurred. Either more liquid must be redosed or the measurement must be repeated.

Basically the difference between the measured value and the reference value can be evaluated. Their ratio is however more advantageous since it reduces eventual disturbing factors. Understandably the ratio of the reference value to the measured value can also be evaluated with then an indication resulting if a threshold value is undershot.

In a preferred embodiment the measuring field is divided into at least two measuring areas which are separately measured, with each measured value being compared with a respectively associated reference value. In this way a non-uniform wetting of the measuring field can be captured.

The previously described methods can also be so carried out that first a first measuring area is measured and that a second measuring area is then first measured if the relationship of the measured value and reference value for the first measuring area reaches or undershoots a pre-given threshold value.

The basic object of the invention can, in a method of the previously mentioned type, also be solved in that within a pre-given amount of time a plurality of measurements are carried out, that each measured value is compared with the measured value taken a given number of measuring steps previously, and that an indication is given if the relationship of the measured value and the comparison measured value exceeds a pre-given threshold value.

Within the reaction time in the case of normal courses of reaction, that is in the case of a sufficient dosing, the reflectivity curve steadily falls. Therefore, normally each measured value is smaller than the previously measured value. If within the reaction time a rise in the measured value takes place this indicates a bleaching of the measuring field because of a too small amount of the liquid to be investigated. Also in this case the measuring field can be divided into several measuring areas which are separately measured, in order to be able to test for an areawise uniform wetting of the measuring field.

Further advantageous embodiments of the invention are given in the further dependent claims.

BRIEF DESCRIPTION OF THE DRAWINGS

The following description in combination with the accompanying drawings explains the invention by way of exemplary embodiments. The drawings are.

DETAILED DESCRIPTION OF THE PREFERRED EMBODIMENTS

Figure 1:
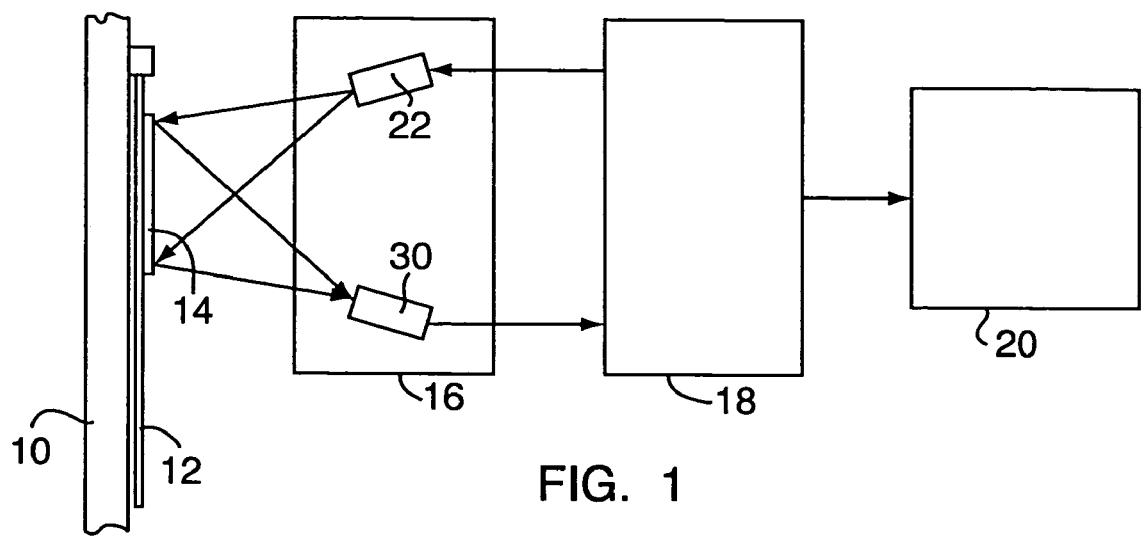
FIG. 1 a schematic illustration of a measuring apparatus according to a first embodiment of the invention, FIG. 2 an illustration according to FIG. 1 showing a second embodiment for dividing the measuring field into different measuring areas, FIG. 3 a schematic plan view of a portion of a test strip and of the measuring field with different measuring areas, FIG. 4 a view similar to FIG. 2 of a modified embodiment, FIG. 5 a graphical illustration of a change of reflectivity with respect to time for explaining the measurement procedure, FIG. 6 a variant of the arrangement illustrated in FIG. 3, and FIG. 7 a further variant of the arrangement illustrated in FIG. 3.
Figure 3:
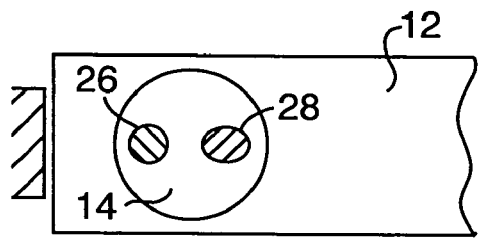

A measuring device suited to the carrying out of the above-explained measurements, as shown in FIG. 1, includes a strip support 10 for a test strip 12 with a measuring field 14, a measuring optic 16, and an evaluation and control circuit 18, as well as indicator unit 20.

The measuring optic includes a light source 22, which for example is formed by a light emitting diode. The light source is directed toward the measuring field 14 of the test strip. The light source is controlled by the evaluation and control circuit 18. The measuring optic 16 further includes a detector 30 which can receive light from the entire measuring field 14. The detector 30 is connected with the evaluation circuit 18.

In the case of a measurement, for example a blood sugar measurement, the patient drops a drop of blood onto the measuring field 14 of the test strip 12 and lays the strip in a pre-given position onto the strip support 10. The measuring field is illuminated and the detector receives the reflected light. Because of the applied blood and a chemical reaction with a test substance inside the test field 14 the reflectivity of the measuring field changes in a definite way. In general the field becomes darker. That is the reflectivity sinks. From the change of the reflectivity, by way of a characteristic curve stored in the evaluation circuit, the blood sugar content can be determined, which is then indicated by the indicator unit 20.

Correct measured values are however only obtained if the measuring field 14 is sufficiently wetted with the liquid under investigation so that the reaction of the investigated material with the test substance inside of the measuring field can run to full completion. To test for this, after a pre-given reaction time the measured value is compared with a reference value in the evaluation circuit 18, which reference value generally is the measured value of the unwetted measuring field. If this comparison shows that the difference between the measured value and the reference value is smaller than a pre-given threshold value or that the ratio between the measured value and the reference value remains above a pre-given threshold value, it must be taken that the measuring field has not been sufficiently wetted so that the test reaction in the measuring field has not substantially been completed, as would correspond to an expected minimum concentration of the substance under investigation. In this case an indication is provided by the indicator device 20 so that the patient has the possibility perhaps to still make a supplemental dosage, or in any event is warned to ignore this measured value and is instructed to repeat the measurement.

Figure 2:
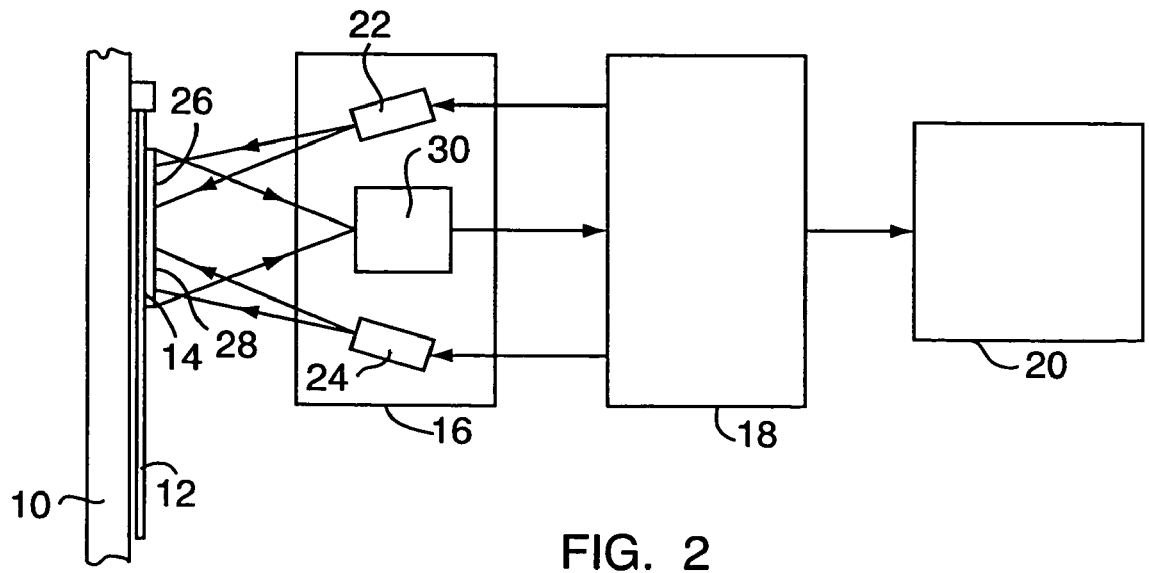

FIG. 2 shows an exemplary embodiment for a measuring apparatus which can separately measure two measuring areas within the measuring field. For this in the apparatus of FIG. 2 a further light source 24 is provided. The light sources 22 and 24 are directed onto separate measuring areas 26 and 28 inside of the measuring field 14, whereas the detector 30 previously captured the entire measuring field 14. The instant measurement for each measuring area 26 and 28 is carried out in the same way as in the embodiment of FIG. 1 and each measurement is compared with the corresponding reference value. If entirely too little liquid is applied to the measuring field 14, then for both measuring areas 26 and 28 the ratio between the measured value and the reference value falls below the pre-given threshold value, so that the indicator device 20 will indicate accordingly. An indication will, however, be given if for only one of the measuring areas the ratio between the measured value and the reference value is too large, whereby a non-uniform wetting of the measuring field is indicated.

Figure 4:
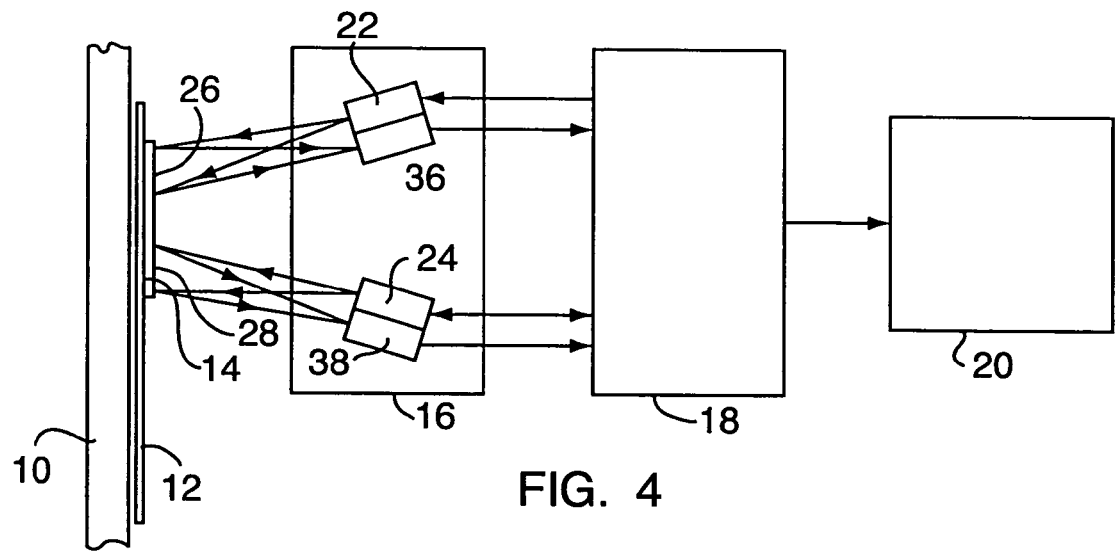

The embodiment according to FIG. 4 differs from that of FIG. 2 only in that instead of one detector being provided for the two light sources 22 and 24 an individual detector 36 and 38 is provided for each light source 22 and 24 respectively. In the embodiment according to FIG. 2 the light sources 22 and 24 have to be operated alternately or following one another. With the embodiment of FIG. 4 the two measuring areas can be measured independently of one another. That is, even at the same time.

Figure 5:
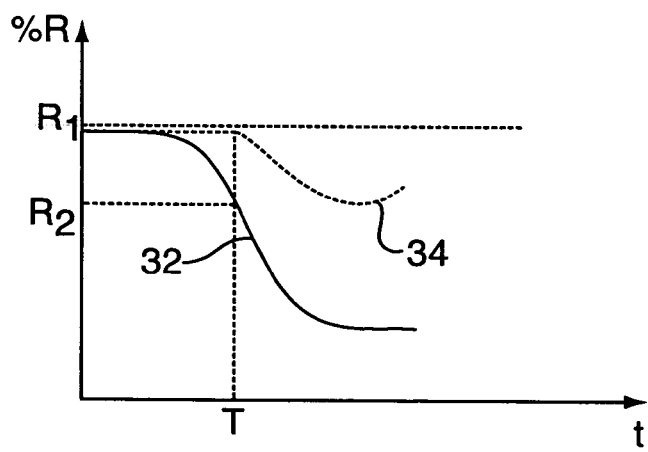

FIG. 5 shows the change in the reflectivity within a measuring area (ordinate) with respect to time (abscissa). The solid curve 32 represents the normal course of the reflectivity with time. This normal course corresponds to a sufficient wetting of the measuring field. The initial value is the value R1, which corresponds to the empty value of the measuring field before the application of blood, and which therefore forms the reference value. The broken line curve 34 illustrates a reflectivity course such as can be gotten from an insufficient wetting of the measuring field within the measuring area. The reaction starts later, is perhaps incomplete, or the reflectivity again increases because the reaction goes no further and the measuring field bleaches. Therefore as an example the difference between the reflectivity value R1 and the reflectivity R2 at a time T does not reach a pre-given threshold value and in this way indicates an insufficient wetting of the measuring field. The same applies if the measured reflectivity at two points of time following one another again increases as indicated by the upwardly directed end of the curve 34.

Figure 6:
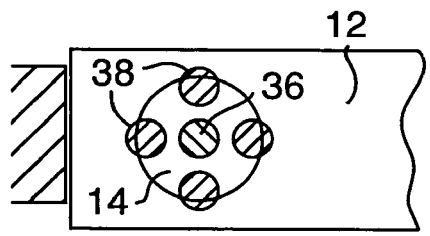

In the variation illustrated in FIG. 6, associated with the test field 14 are a central measuring area 36 and four measuring areas 38 arranged along the circumferential edge of the test field. The measured result of the central measuring area 36 is then only evaluated and utilized if the edgewise measuring areas 38 show at least a minimum value of discoloration. If this is the case, it can therefore be taken that the central measuring area has been sufficiently wetted. In this case the measuring apparatus, as in the FIG. 2 solution, has a number of light sources (LEDs) corresponding to the number of the measuring areas 36, 38 and one detector or, as in the solution of FIG. 4, a number of light source/detector pairs corresponding to the number of measuring areas 36, 38.

Figure 7:
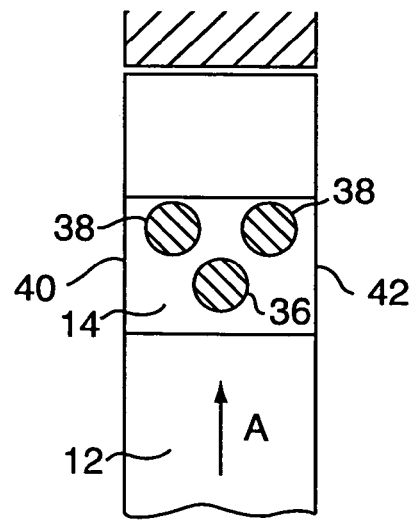

FIG. 7 shows a further variant for the measurement of a test strip. In this case, two edgewise measuring areas 38 are arranged sidewise in front of the central measuring area 36 with respect to the insertion direction of the test strip indicated by the arrow A. This solution is especially suited for test strips with which the liquid to be investigated is delivered through the edges 40, 42, as for example when the test strip is to be dabbed with its edge 40 onto the liquid to be investigated, so that the liquid is sucked up by the carrier material forming the test field. The measuring value obtained from the central measuring area 36 is then only evaluated if both edgewise measuring areas 38 show a change in reflectivity value with respect to the normal value, that is show at least a minimum amount of discoloration. If this is the case, than one can be certain that the fluid to be investigated has sufficiently wetted the central measuring area 36 independently of by which of the edges 40, 42 the investigated fluid has been absorbed.

If only one side edge of the test field is provided for the delivery of the liquid, for example the edge 40, one need only evaluate one edgewise measuring area 38, so that in the case of FIG. 7 the right edge sided measuring area 38 is measured and evaluated. If, however, the liquid on the other hand is delivered through the side edge 42, then in FIG. 7 the left edge sided measuring area 38 has to be measured.

The position of the edgewise measuring areas 38 in front of the central measuring area 36 can be used to control whether the test strip 12 has been inserted into the measuring device up to the stop; that is, has reached its correct measuring position.

The invention claimed is:

1. A method for measuring the concentration of a substance in a liquid, especially for blood sugar measurement, the method comprising the steps of: applying a liquid to a measuring field including a hydrophilic area of a test strip, measuring the optical reflectivity or transmissivity in the measuring field, comparing the measured value of the optical reflectivity or transmissivity in the measuring field at a pre-given time with a reference value, and activating an indicator if a relationship between the measured value and the reference value exceeds a pre-given threshold value.

2. The method according to claim 1 wherein the step of comparing includes using a reference value corresponding to that of an unwetted measuring field.

3. The method according to claim 1, wherein the step of comparing includes using a reference value corresponding to a lowest concentration of the substance to be measured.

4. The method according to claim 1 wherein the step of activating an indicator includes displaying indicia such as "LOW" or "F-1" if the relationship of the measured value to the reference value exceeds the pre-given threshold value.

5. The method according to claim 1 wherein the measuring field includes at least two measuring areas, the step of measuring includes separately measuring each of the measuring areas, and the step of comparing includes comparing a measured value for each of the measuring areas with a reference value associated with the respective measuring area.

6. The method according to claim 5, wherein the step of measuring further includes a first measuring of a first measuring area followed by a first measuring of a second measuring area if the relation between the measured value and the reference value for the first measured area has reached or exceeded a pre-given threshold value.

7. The method according to claim 5, wherein the measured value of the measuring area which first reaches or exceeds the pre-given threshold value is indicated.

8. A method for measuring the concentration of a substance in a liquid, especially for blood sugar measurement, the method comprising the steps of: applying a liquid to be measured to a measuring field of a test strip, measuring the optical reflectivity or transmissivity in the measuring field effected by the liquid, the step of measuring including taking a plurality of measurements in the measuring field within a pre-determined period of time and comparing each measured value with the measured value taken a given number of measurements previously, and activating an indicator when the measured value exceeds the comparison measured value.

9. The method according to claim 8, further comprising a step of activating an indicator if the difference between the measured values compared with one another within a pre-given period of time take on no steady course.

10. The method according to claim 8, further comprising a step of activating an indicator if the differences between the measured values in successive comparisons change in sign.

* * * * *